United States Patent
Roberts

(10) Patent No.: US 12,137,313 B2
(45) Date of Patent: Nov. 5, 2024

(54) EAR INSERT

(71) Applicant: FLARE AUDIO TECHNOLOGIES LIMITED, Lancing (GB)

(72) Inventor: Davies Roberts, Lancing (GB)

(73) Assignee: FLARE AUDIO TECHNOLOGIES LIMITED, Lancing (GB)

( * ) Notice: Subject to any disclaimer, the term of this patent is extended or adjusted under 35 U.S.C. 154(b) by 241 days.

(21) Appl. No.: 17/899,674

(22) Filed: Aug. 31, 2022

(65) Prior Publication Data

US 2022/0417638 A1 Dec. 29, 2022

Related U.S. Application Data

(63) Continuation of application No. PCT/GB2021/050676, filed on Mar. 18, 2021.

(30) Foreign Application Priority Data

Mar. 19, 2020 (GB) ..................... 2004011

(51) Int. Cl.
*H04R 1/10* (2006.01)
*H04R 25/00* (2006.01)

(52) U.S. Cl.
CPC ......... *H04R 1/1016* (2013.01); *H04R 25/652* (2013.01)

(58) Field of Classification Search
CPC ..... H04R 1/1016; H04R 25/652; A61F 11/30; A61F 11/08; A61F 11/085
See application file for complete search history.

(56) References Cited

U.S. PATENT DOCUMENTS

2014/0138179 A1 5/2014 Burton
2017/0065457 A1 3/2017 Ogura et al.

FOREIGN PATENT DOCUMENTS

| CN | 208598633 U | 3/2019 |
| EP | 1937031 A1 | 6/2008 |
| EP | 2809081 A1 | 12/2014 |
| GB | 190116423 A | 1/1902 |

OTHER PUBLICATIONS

PCT International Search Report for PCT/GB2021/050676, filed on Mar. 18, 2021, mailed on May 27, 2021.
PCT Written Opinion for PCT/GB2021/050676, filed on Mar. 18, 2021, mailed on May 27, 2021.
United Kingdom Search Report under Section 17 for United Kingdom Patent Application GB2004011.9, mailed on Aug. 25, 2020.

*Primary Examiner* — Tuan D Nguyen
(74) *Attorney, Agent, or Firm* — Basil M. Angelo; ANGELO IP

(57) ABSTRACT

An ear insert having a funnel-shaped wall defining a tapering channel extending between first and second open ends, the first open end having a diameter greater than that of the second open end, wherein a portion of the funnel-shaped wall adjacent the second open end enables the ear insert to be located within the opening of a user's ear canal, with the first open end adjacent the user's tragus and the second open end facing the user's tympanic membrane, at least a portion of the tapering channel having an acoustic wave reflecting region extending from a location at or near the first open end toward the second open end at an angle of 60°-75° relative to a lateral plane defined by the edge of the funnel-shaped wall at the first open end.

18 Claims, 6 Drawing Sheets

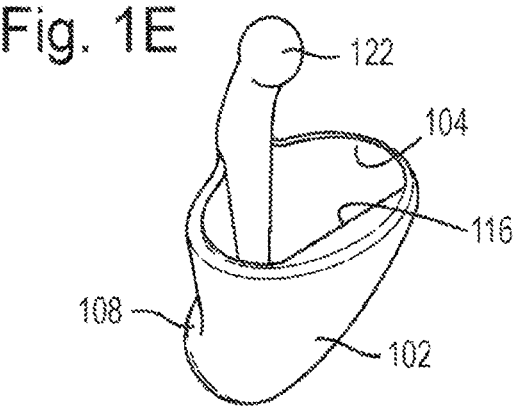
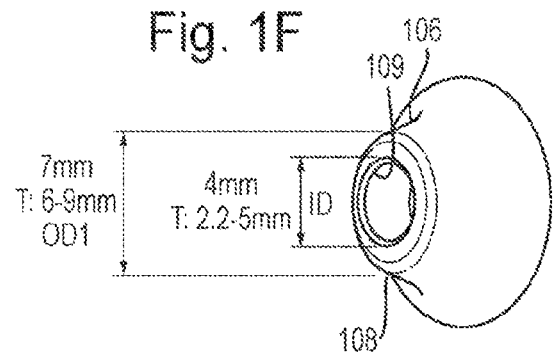

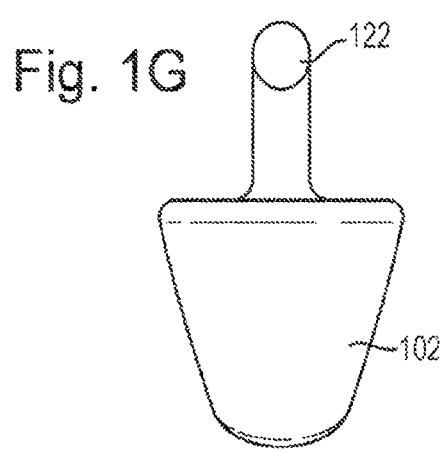
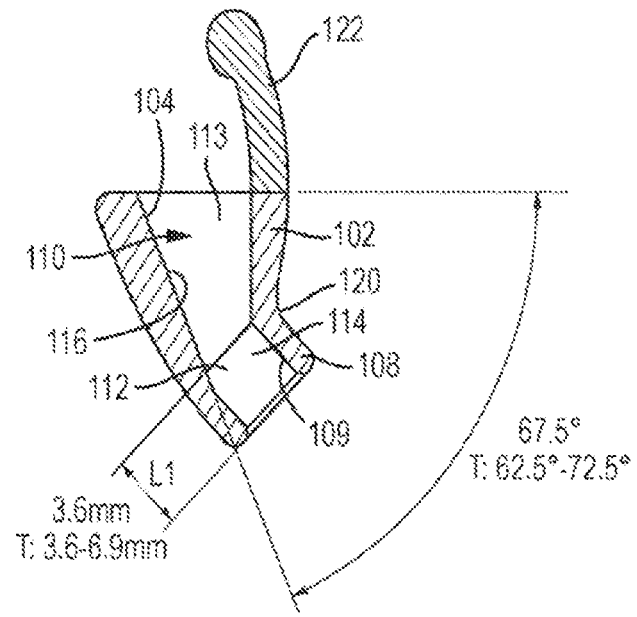

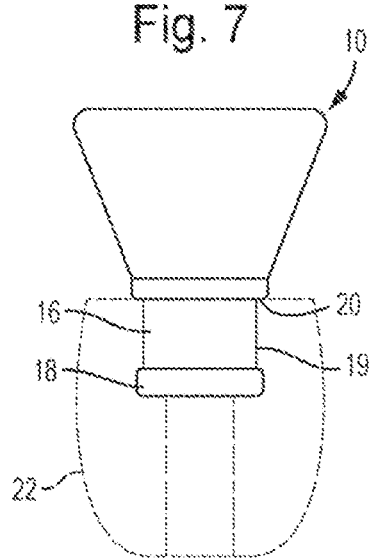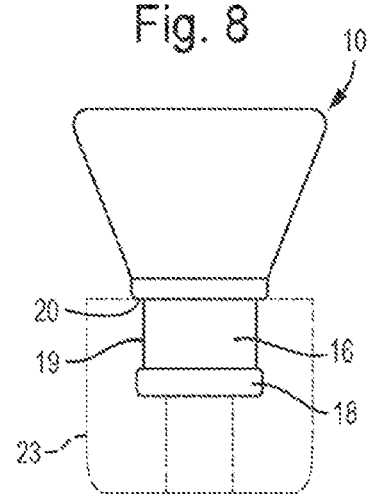

EAR INSERT

CROSS-REFERENCE TO RELATED APPLICATIONS

This application is a continuation of PCT International Application PCT/GB2021/050676, filed on Mar. 18, 2021, which is incorporated by reference in its entirety for all purposes.

TECHNICAL FIELD

This invention relates generally to an ear insert for insertion in an ear and, more particularly to an ear waveguide device for reducing sound distortion caused by resonance within the ear canal.

BACKGROUND OF THE INVENTION

The human ear has three distinguishable parts, namely the outer, middle and inner ear. The outer ear consists of the visible portion called the auricle or pinna which projects from the side of the head. The middle ear is a narrow, air-filled cavity known as the ear canal leading from the outer ear to the inner ear, the inner end of the ear canal being dosed by a tympanic membrane so as to form a boundary between the middle ear and the inner ear. The outer ear is shaped to form an irregular shallow funnel, with a depression known as the concha leading directly to the entrance of the ear canal. The concha is partly covered by two small projections, the tongue-like tragus in front and the antitragus behind.

The function of the outer ear is to collect sound waves and guide them, via the ear canal, to the tympanic membrane. In effect, the outer ear acts to 'funnel' sound waves from a listener's vicinity into the ear canal. The ear canal is essentially a tube that is open at one end (the concha region) and closed at the other end (tympanic membrane). The air inside the ear canal acts as a resonating body. The natural resonant frequency of the ear canal is four times its length (~25 mm average for an adult) and, therefore, it acts as a quarter-wave resonator and amplifies sound waves. Thus, sound waves enter the ear canal, where they are amplified as they travel through the ear canal until they reach the tympanic membrane and are transmitted to the inner ear. However, the geometry of the outer ear, including the concha, creates an interference in the sound waves as they are 'funnelled' into the ear canal, and this interference, characterized by an incoherent sound wave, is amplified with a gain up to 20 dB at some frequencies, and presents at the tympanic membrane as noise distortion, which can have a negative and detrimental effect on the quality of sounds, such as music, reaching the inner ear.

Furthermore, it has been documented that noise (i.e. intrusive or unwanted sound that disrupts, distracts or detracts from regular functioning) causes stress and can have a negative effect on health and productivity. The Vagus nerve, together with the parasympathetic nervous system, is responsible for (amongst other things) triggering the human fight-or-flight stress response. it follows, therefore. That noise can trigger the fight-or-flight response and cause stress. The inventor has discovered that noise distortion created by the geometry of the concha and amplified (especially at frequencies above ~1.5 kHz) within the ear canal can cause the Vagus nerve to trigger the tight-or-flight stress response. Given that a human being almost constantly receives sound waves from various sources during their day-to-day lives, they are regularly receiving distorted sound amplified at a gain of up to 20 dB at the tympanic membrane, and this amplified distorted sound can cause triggering by the Vagus nerve of the fight-or-flight stress response. It follows, therefore, that the average human being may be regularly and persistently in a state of elevated stress, simply due to noise distortion of the type described above.

Clearly, then, there is a desire to reduce the occurrence of noise distortion created and amplified within the human ear canal, without necessarily reducing the quality or volume of the true sound waves reaching the tympanic membrane.

BRIEF SUMMARY OF THE INVENTION

In accordance with a first aspect of the present invention, there is provided an ear insert which has a generally funnel-shaped wall defining a tapering channel extending between first and second open ends, the first open end having a diameter or width greater than that of the second open end, wherein a portion of the funnel-shaped wall immediately adjacent the second open end is configured to enable the ear insert to be located within the opening of a user's ear canal, for use, with the first open end adjacent the user's tragus and the second open end facing the user's tympanic membrane, at least a portion of the tapering channel comprising an acoustic wave reflecting region that extends from a location at or near the first open end toward the second open end at an angle of between 60° and 75° relative to a lateral plane defined by the edge of the funnel-shaped wall at the first open end.

In an exemplary embodiment, the acoustic wave reflecting region extends from a location at or near the first open end toward the second open end at an angle of between 65° and 70°, and optionally between 62° and 63°, relative to the lateral plane defined by the edge of the funnel-shaped wall at the first open end.

Beneficially, and in accordance with specific exemplary embodiments, the ear insert may be configured to fit onto or over an ear bud of in-ear headphones. In an exemplary embodiment, the ear insert may be shaped and configured at the second open end to receive and retain a resilient tip.

The acoustic wave reflecting region may, optionally, comprise a substantially planar surface.

In one embodiment, the portion of the funnel-shaped wall immediately adjacent the second open end may comprise a generally tubular portion having a longitudinal axis extending at an angle relative to the lateral plane defined by the edge of the funnel-shaped wall at the first open end, the second open end being at the distal end of the tubular portion. Beneficially, the longitudinal axis of the generally tubular portion may extend at an angle of between 40° and 50°, e.g. substantially 45°, relative to the lateral plane defined by the edge of the funnel-shaped wall at the first open end.

Beneficially, the tubular portion may he configured to be inserted into an ear canal, for use, with the second open end facing the user's tympanic membrane and the first open end facing generally rearwardly of the user. Accordingly, the outer diameter of the tubular portion may be between 5 and 8 mm, and the diameter of the second open end may be between 2 and 5 mm.

In an exemplary embodiment the outer profile of the funnel-shaped wall may comprise a rounded convex region extending from an edge adjacent the first open end to an edge adjacent the second open end, and an opposing concave region at the proximal end of the tubular portion, between the first and second open ends. In this case, the concave region defines a front of the ear insert and the convex surface diametrically opposite defines the rear of the insert, when in use, and the overall length of the funnel-shaped wall may be configured such that, in use, with the tubular portion partly inserted in a user's ear canal, the edge of the first open end at the rear of the ear insert lies adjacent the inner surface of the user's tragus. Beneficially, therefore, the overall length of the funnel-shaped wall may he between 7 and 17 mm, and optionally between 10 and 12 mm for an average adult.

In a preferred embodiment, a length or the diameter of the first open end may be at least double a length or the diameter of the second open end.

In an exemplary embodiment, the second open end may be generally elliptical.

In this case, the length of the first open end may be between 9.5 and 18 mm and the width of the first open end may be between 7 and 13 mm.

in a first exemplary embodiment, the ear insert may be integrally moulded of a resiliently deformable material. In a second exemplary embodiment, at least the acoustic wave reflecting region may be formed of a rigid material. For example, the ear insert may comprise an inner member formed of rigid material and defining the tapering channel, and an outer sleeve formed of a rigid or resiliently deformable material. Alternatively, the ear insert may be integrally formed of a rigid material, such as plastic, wood or metal.

in other exemplary embodiments, the tapering channel may communicate, at its narrower end, with a coaxial tube, the inner surfaces of the tapering channel and of the tube being surfaces of revolution about a common longitudinal axis, and the outer surface of the tube defining at least one circumferential ridge or groove, wherein the inner surface of the tube has a diameter of at least 2.5 mm, the outer surface of the tube has a diameter of no more than 10 mm, and the overall length of the insert is no more than 17 mm.

in this case, the tapering channel may be conical, at least along part of its length, and the angle between the opposed conical surfaces may be between 30° and 60°, and more preferably between 40° and 50°.

The tapering channel may, optionally, have a. curved longitudinal shape. For example, the tapering channel may be flared, such that as the diameter decreases, the angle between a tangent to the inner surface and the longitudinal axis also decreases.

In some exemplary embodiments, the narrow end of the tapering channel may have a curved longitudinal shape such that the inner surface of the tube is tangential to the curved longitudinal shape where they meet.

The inner surface of the tube may have a diameter of at least 2.2 mm, but less than 6.0 mm, and the outer surface of the tube may have a diameter of no more than 8 mm.

The overall length of the insert may be between 7 and 16.5 mm, and the length of the tube may be between 25% and 50% of the overall length of the insert.

Optionally, at the wider end of the tapering channel, the external diameter may be between 9 mm and 18 mm.

in some preferred embodiments, the dimensions of the ear insert may be such that when the tube, carrying a resilient tip, is inserted into the ear canal, in use, the outer end does not project beyond the tragus

BRIEF DESCRIPTION OF THE DRAWINGS

Embodiments of the present invention will now he described by way of examples only and with reference to the accompanying drawings, in which:

FIG. 1E is a schematic side perspective view of the ear insert of FIG. 1A;

FIG. 1F is a schematic illustration of the tip of an ear insert according to an exemplary embodiment of the present invention;

FIG. 1G is a schematic rear view of the ear insert of FIG. 1A;

FIG. 2 is a schematic side cross-sectional view of an ear insert according to an exemplary embodiment of the invention;

DETAILED DESCRIPTION OF THE INVENTION

Figure 1A:
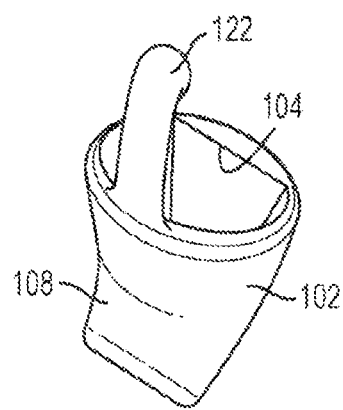
FIG. 1A is a front schematic perspective view of an insert according to an exemplary embodiment of the invention.
Figure 1B:
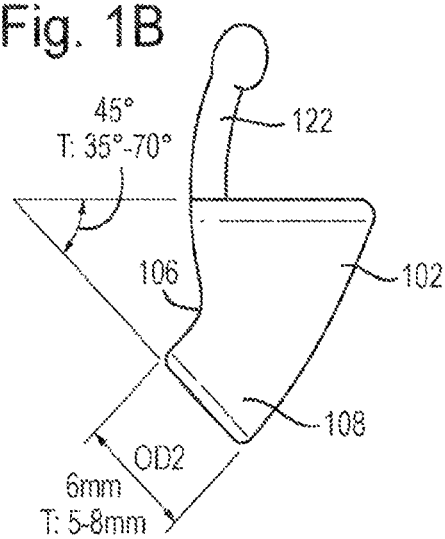
FIG. 1B is a schematic side view of the ear insert of FIG. 1A.
Figure 1C:
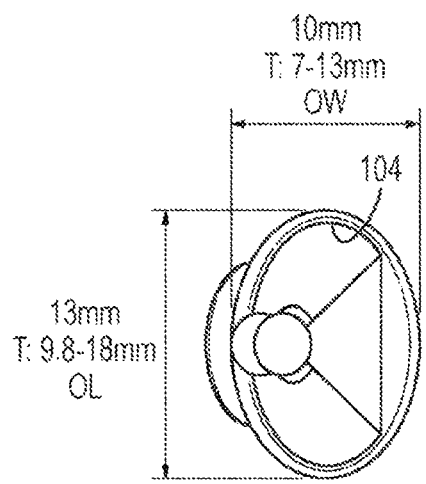
FIG. 1C is a schematic rear perspective view of the ear insert of FIG. 1A.
Figure 1D:
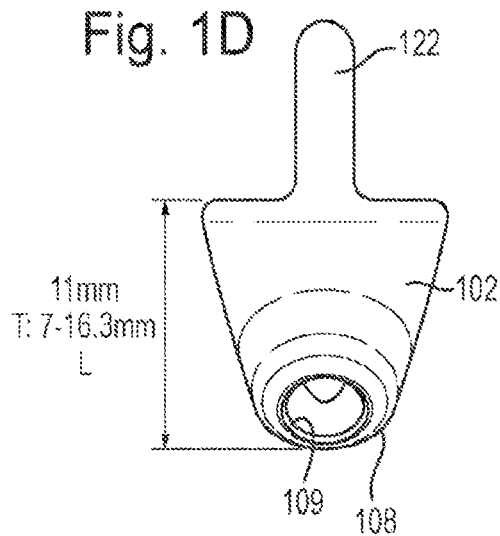
FIG. 1D is a schematic front view of the ear insert of FIG. 1A.

Directional descriptors such as upper, lower, left, right, clockwise, anti-clockwise, front, rear and other similar adjectives are used for clarity and refer to the orientation of the invention as illustrated in the drawings, however it will be clear to those skilled in the art that the invention may not always be oriented as illustrated and the invention is not intended to be limited in this regard.

Referring to FIGS. 1A to 1G of the drawings, there is illustrated an ear insert 100 according to a. first exemplary embodiment of the present invention. The ear insert 100 comprises a single piece of moulded silicone or other mouldable and resiliently deformable plastics material. The insert comprises a generally rounded outer profile having two integral portions. A first tubular portion 102 has a generally oval cross-section and an open first end 104. The outer lateral width OW (FIG. 1C) of the first tubular portion 102 at the open first end 104 is in the range 7 to 1.3 mm, for example 10 mm for an average adult, and the outer lateral length OL (FIG. 1C) is in the range 9.8 to 18mm, for example, 13 mm for an average adult. The dimensions of the first tubular portion gradually decrease along its length and at the opposing second end 106, the outer diameter ODI (FIG. 1F) may be in the range 6 to 9 mm, for example, 7 mm for an average adult. An integral second tubular portion 108 extends from the second end 106 of the first tubular portion 102 such that its longitudinal axis is at a 35-70°, e.g. 45° angle to the longitudinal axis of the first tubular portion 102. The outer profile of the insert is convex and relatively gently rounded on one side (the 'rear') to accommodate the angle between the first and second tubular portions 102, 108 and, on the other side (the 'front'), the angle is accommodated by a rounded hut relatively sharp concave 'corner' between the first and second tubular portions. The second tubular portion 108, which is open at its distal end 109, is of generally circular cross-section and has an outer diameter 0D2 (FIG. 1E) in the range 5 to 8 mm, for example, 6 mm for an average adult and length L1 (FIG. 2) in the range 3.6 to 6.9 mm, for example, 3.6 mm for an average adult. It will be appreciated that the various dimensions can be altered within the ranges given to suit smaller or larger ears, and even child's sizes, as required.

Referring additionally to FIG. 2 of the drawings, the first and second integral portions 102, 108, together, define a continuous channel 110 therethrough which, itself, is comprised of two portions: the first channel portion 112 being defined through the first tubular portion 102 and the second channel portion 114 being defined through the second tubular portion 108. The first channel portion is defined, along the 'front' and 'sides' by the oval-shaped rounded profile of the first tubular portion 102. However, the 'rear' wall of the first tubular portion 102 is thicker than the remaining walls so as to provide a 'rear' channel portion 112 that is substantially flat so as to provide a planar surface 116. As shown in FIG. 2 of the drawings, when the insert 100 is in an 'upright' position, with the lateral plane of the first open end 104 being horizontal, the planar surface 116 of the first channel portion 113 extends at an acute angle, greater than 45°, toward the second channel portion 114, and the diameter or width of the first channel portion 113 reduces from the open end 104 to the junction with the second channel portion 114 defined by the second tubular portion 108. The angle of the planar surface 116, relative to horizontal defined by the lateral plane of the first open end 104 may be in the range 62.5 to 72.5°, for example, 67.5° for an average adult.

As described above, and best illustrated by FIG. 2, the angled configuration of the second tubular portion 108 relative to the first tubular portion 102 is accommodated at the 'rear' and 'sides' of the insert by a gently rounded outer wall that curves from the first open end 104 to the distal second open end 109 defined by the second tubular portion 108. As stated above, the length L1 (FIG. 2) of the second tubular portion 108 is in the range 3.6 mm to 6.9 mm, for example, 3.6 mm for an average adult. The diameter ID (FIG. 1F) of the distal open end 109 may be in the range 2.2 mm to 5 mm, for example, 4 mm for an average adult. It will he appreciated that, whilst the open end 109 of the second tubular portion 108 is illustrated as being generally circular in this exemplary embodiment, it may have an alternative shape and configuration. For example, it may be generally oval or 'slit-like' in other exemplary embodiments and the present invention is not necessarily intended to he limited in this regard. The thickness of the 'front' and 'side' walls of the second tubular portion 108 are substantially constant along the length to the junction between the first and second tubular portions 102, 108, defined by the concave rounded 'corner' 12.0. However, whilst the diameter of the second channel portion 114 is substantially constant from the distal open end 109 along a portion of the length of the second tubular portion 108, it tapers inwardly (by means of a thickening of the rear wall of the second tubular portion 108) along a short portion toward the junction between the first and second tubular portions 102, 108, such that that short portion of the inner rear wall of the second channel portion 114 forms an extension of the planar surface 116 defining the 'rear' wall of the first channel portion 113.

An elongate tab 122 may be provided, extending from the rim of the first tubular portion 102, at its open end 104, to facilitate insertion of the device into, and removal of the device from, a user's ear.

In the exemplary embodiment described above, the ear insert 100 is integrally moulded from a resiliently flexible material such as silicone. However, in an alternative exemplary embodiment, the insert 100 may have a two-part configuration. In this case, the device may comprise a metal (e.g. stainless steel or titanium) insert providing defining the first and second channel portions 113, 114 (i.e. the channel including the planar surface 116) and an outer sleeve, formed of a resiliently flexible material such as foam or silicone, defining the curved outer profile to enable the device to be comfortably fitted within a user's ear. The reduction in noise distortion when the planar (reflecting) surface 116 is formed of a rigid material can thus be further increased, in use, the ear insert 100 is inserted into a user's ear at the open end of the ear canal (adjacent the concha region) such that the second tubular portion extends into the ear canal (with the distal open end 109 facing the tympanic membrane at the other end of the ear canal), and the rounded 'rear' surface of the first tubular portion 102 resting at or just behind the tragus, with the first open end 104 facing backward.

It will be appreciated that the outer diameter (OD2) of the second tubular portion 108 is designed, in this example, to be around the same as that of the entrance of the ear canal (external auditory canal) of an average adult. The overall length of the insert 100 (excluding the tab 122) is approximately equal to the average length of the external auditory canal of an average adult, wherein the external auditory canal comprises the ear canal extending from the tragus to the middle ear. As a result, the insert 100 can be fully inserted into the external auditory canal, with the outer edge of the first tubular portion 102 resting against the rear (inner) surface of the tragus and the second tubular portion 108 extending a short way into the ear canal, with the distal open end 109 facing the tympanic membrane.

As described above, at least the outer wall of the insert 100 is beneficially formed of a soft, resiliently deformable material, such as silicone, so that it can be compressed sufficiently to be inserted into the ear and then released back to its original form, once inserted, to fit snugly within the ear. In the example illustrated in FIGS. 1A to 1G and 2, the insert (including the profiled inner channel) is integrally formed of a mouldable material such as silicone. However, and as stated above, in alternative embodiments, the device may comprise an inner member defining the profiled inner channel including the planar surface 116, and an outer sleeve member around the inner member, In this case, the inner member may be formed of a rigid material such as plastic or metal (e.g. stainless steel or titanium), and the sleeve member could be formed of a resiliently deformable material such as silicone, to provide a comfortable snug fit, in use, The angle defined by the longitudinal axis of the second tubular portion 108 is at substantially 45° to the diametric plane defined between the rim around the first open end 104, and the angle of the planar surface 116 provided at the 'rear' inner surface of the first channel portion 113 (and a small portion of the second channel portion 114) is at substantially 22.5" relative to the longitudinal axis of the second tubular portion 108. The inventor has discovered that these relative angles, and especially the angle of the planar reflecting surface 116 relative to the first and second open ends 104, 109 of the insert, can provide optimum results in adults with average ear dimensions. Furthermore, and as stated previously, all dimensions, especially the outer dimensions of the tubular portions 102, 108, can be adjusted (particularly within the tolerances provided) to accommodate, for example, children's ear dimensions, or adults having larger or smaller external auditory canals.

Once the device is in situ, with the distal open end 109 of the second tubular portion 108 located in the ear canal facing the tympanic membrane, and the 'upper' edge of the first tubular portion 102 resting against the rear (inner) surface of the tragus, with the first open end 104 facing backward, it effectively acts to minimise or even eliminate the effect of the concha on sound waves entering the ear. The device still 'funnels' sound waves into the ear canal, due to its tubular shape and configuration, having a first open end 104 of width over double the diameter of the second, distal end 109. The angled planar surface 116 acts to minimise the number of times sound waves reaching the external auditory canal are reflected before they reach the tympanic membrane. Given that it is these reflections that create incoherence in the sound waves, and it is this incoherence that represents distortion or 'noise' that is then amplified within the ear canal, it will be clear that the device, in use, acts to reduce distortion in sound waves reaching the tympanic membrane. Without the device, sound waves from a listener's vicinity reach the external auditory canal in the concha region which defines surfaces that can be at up to 90° relative to the longitudinal axis of the ear canal (leading to the tympanic membrane). Thus, sound waves reaching the external auditory canal must change direction by up to 90° to reach the tympanic membrane. However, sound waves, especially those over around 1.5 kHz which are not highly diffracted, can only 'change direction' in this manner by repeated reflection within the concha region, until they are oriented to enter the ear canal. The configuration of the external auditory canal, with its grooves and ridges, is such that these sound waves can be reflected many times before entering the ear canal, These reflections result in result in primarily incoherent sound waves entering the ear canal and such incoherent sound waves (representing significant distortion or 'noise') are amplified within the ear canal before they reach the tympanic membrane. In contrast, the ear insert of the present invention acts to 'funnel' more coherent sound waves into the ear canal, with significantly less reflections, thereby reducing distortion (or 'noise') by up to 8% or more. If the user is wearing the insert whilst listening to music, for example through headphones as described above, the quality and clarity of the music heard by the listener is notably improved. Furthermore, and most surprisingly, if a user is wearing the insert(s) whilst conducting their normal day to day lives, the significant reduction in noise distortion provided by the insert(s) acts to reduce instances of triggering, by the Vagus nerve, of the fight-or-flight stress response. Thus, by wearing the insert of the present invention (preferably one in each ear), the user experiences a calming effect, in that stress is reduced during their normal day-to-day lives.

Figure 3A:
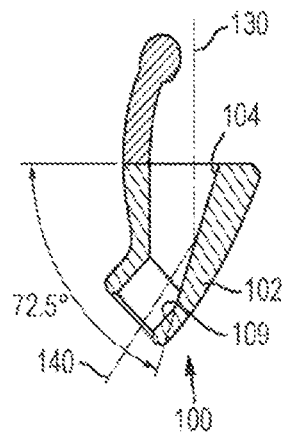
FIG. 3A is a schematic side cross-sectional view of an ear insert according to an exemplary embodiment of the invention.
Figure 3B:
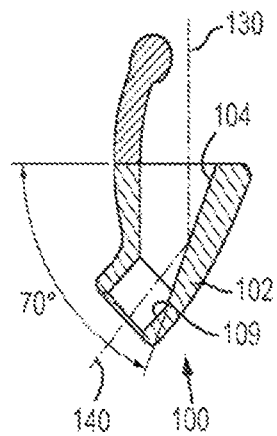
FIG. 3B is a schematic side cross-sectional view of an ear insert according to an exemplary embodiment of the invention.
Figure 3C:
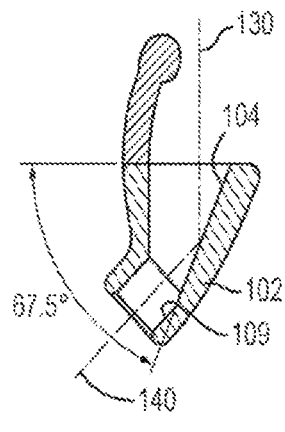
FIG. 3C is a schematic side cross-sectional view of an ear insert according to an exemplary embodiment of the invention.
Figure 3D:
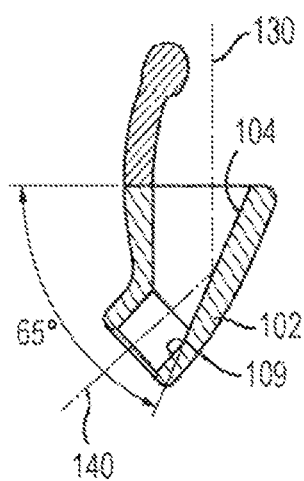
FIG. 3D is a schematic side cross-sectional view of an ear insert according to an exemplary embodiment of the invention.
Figure 3E:
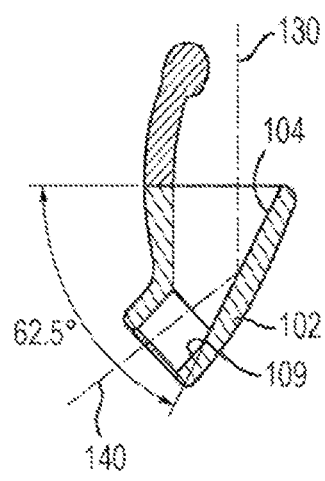
FIG. 3E is a schematic side cross-sectional view of an ear insert according to an exemplary embodiment of the invention.

Referring to FIGS. 3A to 3E of the drawings, the effect of the planar (reflecting) surface 116 within the channel is illustrated schematically. In FIG. 3A, the incoming sound wave 130 enters the first channel portion 113 at an angle of 72.5° relative to the 'horizontal' defined by the plane of the first open end 104 of the insert 100. is illustrated, the incident sound wave 130 hits the reflecting surface 116 within the first tubular portion 102. of the device 100 and the resultant reflected sound wave 140 is directed straight through the second opening 109 toward the tympanic membrane. Thus, only a single coherent sound wave enters the ear canal.

Similarly, and as shown in FIGS. 3B to 3E, incident sound waves 130 at an angle of 70°, 67.5°, 65°, and 62.5° respectively, are reflected by the reflecting surface 116 straight through the second opening 109 in the insert 100 toward the tympanic membrane.

In the embodiment described above, the ear insert is a stand-alone device for use in improving the quality and clarity of sound heard by a user, who may or may not be wearing headphones. In alternative embodiments, an insert of the present invention may he configured to be fitted over each of the integral ear buds of a set of wireless headphones, or as a tip for any existing ear phones with tube output. In yet another exemplary embodiment, an insert according to the invention may be configured to be fitted with resiliency deformable tip, such as that used in conventional earplugs and in-ear headphones, as will be described in more detail below.

Figure 4:
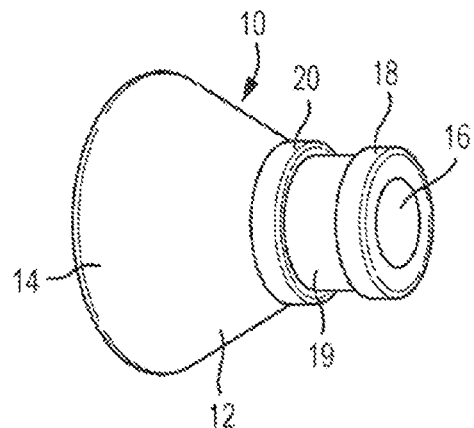
FIG. 4 is a schematic front perspective view of an ear insert according to an exemplary embodiment of the invention.
Figure 5:
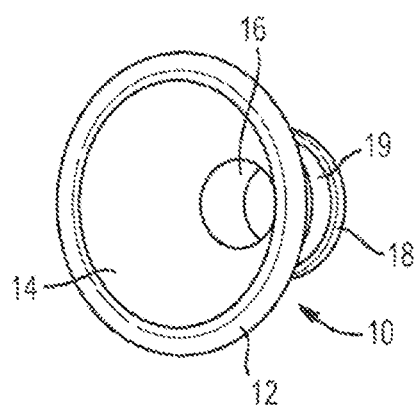
FIG. 5 is a schematic rear perspective view of the ear insert of FIG. 4.
Figure 6:
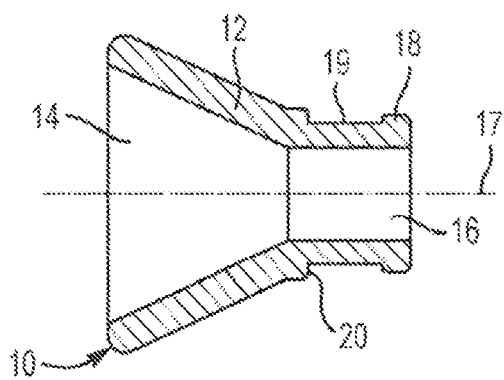
FIG. 6 is a schematic side cross-sectional view of the ear insert of FIG. 4.

Thus, referring to FIGS. 4 to 6 of the drawings, an ear insert 10 according to the second exemplary embodiment may be described as generally in the shape of a. funnel, as it consists of a tubular wall 12 which at one end defines a tapering channel 14 and at the other end defines a tube 16, the tapering channel 14 and the tube 16 having a common longitudinal axis 17 (shown in FIG. 6). The narrow end of the tapering channel has the same internal diameter as the tube 16. In this example, the tapering channel is conical, and the angle between the opposed conical surfaces is 45"

The tubular wall 12 is of substantially uniform thickness, so the outer surface of the wall 12 that defines the conical tapering channel 14 is also conical, but the outer surface of the tube 16 defines a circumferential ridge 18 adjacent the open end of the tube 16 and defines a circumferential step 20 adjacent to the transition between the tube 16 and the tapering channel 14, so there is a circumferential recess 19 between the ridge 18 and the step 20. In this example, the internal diameter of the tube 16 is 3.5 mm, and the external diameter of the ridge 18 is 5.5 mm. In this example, the overall length of the ear insert 10 is 12 mm.

It will be appreciated that an ear insert of the invention may differ in some details from the ear insert 10 of this exemplary embodiment. For example, there may be a gradual transition between the inner surfaces of the tapering channel and of the tube, rather than an abrupt transition; indeed the tapering channel my have a longitudinally curved shape along its length, for example, being flared like a trumpet bell, rather than being conical.

Referring now to FIGS. 7 and 8 of the drawings, before use, the user would provide the ear insert 10 with a tubular and resilient silicone or foam tip, as customarily use with earphones. A tip 22 with a rounded end is shown in broken lines in FIG. 7, whilst a shorter and less rounded tip 23 is shown in broken lines in FIG. 8. In each case, the tip 22, 23 is tubular, and one end of the tip 22, 23 fits tightly over the tube 16, engaging with the circumferential ridge 18 and the 19, and with the end of the tip 22 or 23 abutting the step 20. The tip 22 or 23 is consequently attached securely to the ear insert 10.

The user would then insert the ear insert 10 and the tip 22 or 23 into their ear, with the tip 22 or 23 and the tube 16 fitting into the user's ear canal, and the edge of the open end of the tapering channel 14 sitting behind the tragus. The wall of the tapering channel 14 may act to bend the tragus of the user's ear to one side. Typically, the user would insert two such ear inserts, one in each ear. The overall length of the ear insert 10 is such that after insertion, the outer end of the ear insert is approximately flush with the outer surface of the tragus, so the ear insert 10 does not project from the ear, and is not prominent.

Once again, the shape and configuration of the ear insert 10 acts to 'funnel' sound waves from the vicinity of the user into the ear canal and toward the tympanic membrane. The gradient of the tapering channel 14 is such that an incident sound wave may only be reflected once before reaching the tympanic membrane, thus reducing distortion and improving the clarity and quality of sound heard by the user. If the user uses headphones, it will be appreciated that any sound from the headphone which is incident parallel to the longitudinal axis 17 can follow an unobstructed straight path into the inner part of the ear canal. This has the effect of enhancing the clarity of the sound.

It will be apparent to a person skilled in the art, from the foregoing description, that modifications and variations can be made to the described embodiments without departing from the scope of the invention as defined by the appended claims.

What is claimed is:

1. An ear insert which has a generally funnel-shaped wall defining a tapering channel extending between first and second open ends, the first open end having a diameter or width greater than that of the second open end, wherein a portion of the funnel-shaped wall immediately adjacent the second open end is configured to enable the ear insert to be located within the opening of a user's ear canal, for use, with the first open end adjacent the user's tragus and the second open end facing the user's tympanic membrane, at least a portion of the tapering channel comprising an acoustic wave reflecting region that extends from a location at or near the first open end toward the second open end at an angle of between 60° and 75° relative to a lateral plane defined by the edge of the funnel-shaped wall at the first open end and wherein the acoustic wave reflecting region comprises a substantially planar surface.

2. An ear insert according to claim 1, wherein said acoustic wave reflecting region extends from a location at or near the first open end toward the second open end at an angle of between 65° and 70° relative to the lateral plane defined by the edge of the funnel-shaped wall at the first open end.

3. An ear insert according to claim 1, configured to fit onto or over an ear bud of in-ear headphones.

4. An ear insert according to claim 1, being shaped and configured at the second open end to receive and retain a resilient tip.

5. An ear insert according to claim 1, wherein a portion of the funnel-shaped wall immediately adjacent the second open end comprises a generally tubular portion having a longitudinal axis extending at an angle relative to the lateral plane defined by the edge of the funnel-shaped wall at the first open end, the second open end being at the distal end of the tubular portion.

6. An ear insert according to claim 5, wherein the longitudinal axis of the generally tubular portion extends at an angle of between 40° and 50° relative to the lateral plane defined by the edge of the funnel-shaped wall at the first open end.

7. An ear insert according to claim 5, wherein the longitudinal axis of the generally tubular portion extends at an angle of substantially 45° relative to the lateral plane defined by the edge of the funnel-shaped wall at the first open end.

8. An ear insert according to claim 5, wherein the outer profile of the funnel-shaped wall comprises a rounded convex region extending from an edge adjacent the first open end to an edge adjacent the second open end, and an opposing concave region at the proximal end of the tubular portion, between the first and second open ends.

9. An ear insert according to claim 8, wherein the concave region defines a front of the ear insert and the convex surface diametrically opposite defines the rear of the insert, when in use, and wherein the overall length of the funnel-shaped wall is configured such that, in use, with the tubular portion partly inserted in a user's ear canal, the edge of the first open end at the rear of the ear insert lies adjacent the inner surface of the user's tragus.

10. An ear insert according to claim 5, wherein a length or the diameter of the first open end is at least double a length or the diameter of the second open end.

11. An ear insert according to claim 5, wherein the second open end is generally elliptical.

12. An ear insert according to claim 5, wherein at least the acoustic wave reflecting region is formed of a rigid material, the ear insert comprising an inner member formed of rigid material and defining the tapering channel, and an outer sleeve formed of resiliently deformable material.

13. An ear insert according to claim 1 which is integrally moulded of a resiliently deformable material.

14. An ear insert according to claim 1, wherein the tapering channel communicates, at its narrower end, with a coaxial tube, the inner surfaces of the tapering channel and of the tube being surfaces of revolution about a common longitudinal axis, and the outer surface of the tube defining at least one circumferential ridge or groove, wherein the inner surface of the tube has a diameter of at least 2.5 mm, the outer surface of the tube has a diameter of no more than 10 mm, and the overall length of the insert is no more than 17 mm, and wherein the angle between the opposed conical surfaces is between 30° and 60°.

15. An ear insert according to claim 14, wherein the tapering channel has a curved longitudinal shape, and is flared, such that as the diameter decreases, the angle between a tangent to the inner surface and the longitudinal axis also decreases.

16. An ear insert according to claim 14, wherein the narrow end of the tapering channel has a curved longitudinal shape such that the inner surface of the tube is tangential to the curved longitudinal shape where they meet.

17. An ear insert according to claim 14, wherein the length of the tube is between 25% and 50% of the overall length of the insert.

18. An ear insert according to claim 14, wherein the dimensions of the ear insert are such that when the tube, carrying a resilient tip, is inserted into the ear canal, in use, the outer end does not project beyond the tragus.

* * * * *